(12) United States Patent
Kawamoto et al.

(10) Patent No.: US 9,220,850 B2
(45) Date of Patent: Dec. 29, 2015

(54) INJECTION NEEDLE ASSEMBLY AND DRUG INJECTION DEVICE

(75) Inventors: Hideo Kawamoto, Yamanashi (JP); Tetsuya Oyauchi, Yamanashi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 339 days.

(21) Appl. No.: 13/638,534

(22) PCT Filed: Mar. 3, 2011

(86) PCT No.: PCT/JP2011/054852
§ 371 (c)(1),
(2), (4) Date: Dec. 28, 2012

(87) PCT Pub. No.: WO2011/122224
PCT Pub. Date: Oct. 6, 2011

(65) Prior Publication Data
US 2013/0096502 A1    Apr. 18, 2013

(30) Foreign Application Priority Data
Mar. 30, 2010    (JP) ................. 2010-077107

(51) Int. Cl.
*A61M 5/46* (2006.01)
*A61M 5/32* (2006.01)
*A61M 5/42* (2006.01)

(52) U.S. Cl.
CPC ............... *A61M 5/46* (2013.01); *A61M 5/3287* (2013.01); *A61M 5/42* (2013.01)

(58) Field of Classification Search
CPC ........ A61M 5/46; A61M 5/3287; A61M 5/42
USPC ........................................................ 604/117
See application file for complete search history.

(56) References Cited

U.S. PATENT DOCUMENTS 2,876,770 A * 3/1959 White ........................... 604/198

4,373,526 A    2/1983 Kling
(Continued)

FOREIGN PATENT DOCUMENTS

JP    28-11694 Y1    11/1953
JP    56-500914 A    7/1981
(Continued)

OTHER PUBLICATIONS

Richard T. Kenny, et al., "Dose Sparing with Intradermal Injection of Influenza Vaccine", New England Journal of Medicine, Nov. 25, 2004, pp. 2295-2301, vol. 351, No. 22.

*Primary Examiner* — Theodore Stigell
(74) *Attorney, Agent, or Firm* — Sughrue Mion, PLLC

(57) ABSTRACT

Objects are to ensure a required depressing force and puncture speed when a needle tube is punctured in the skin, and to be able to reliably situate a needle tip of a needle tube in the upper layer of skin. A needle injection assembly 2 includes a needle tube 5 having a needle tip 8 that can be punctured in a living body, a hub 6 that holds the needle tube 5, an adjustment section 12, a stabilizing section 13, and a puncture speed securing member 7. The adjustment section 12 is provided around the periphery of the needle tube 5 and has a needle projection surface 12*a*, from which the needle tip 8 of the needle tube 5 projects. The stabilizing section 13 extends from the hub 6, is disposed to surround the needle tube 5 and has an end face 13*a* that comes in contact with the skin when the needle tube 5 is punctured in the living body. The puncture speed securing member is provided at the adjustment section 12 or stabilizing section 13 such that the puncture speed securing member moves along the axial direction of the needle tube 5. The puncture speed securing member 7 is brought into contact with the skin ahead of the needle tip 8 of the needle tube 5 when the needle tube 5 is punctured in the living body and ensures the speed and depressing force as desired when the needle tube 5 is punctured in the living body.

11 Claims, 6 Drawing Sheets

(56) References Cited

U.S. PATENT DOCUMENTS

| | | | |
|---|---|---|---|
| 5,873,856 A | 2/1999 | Hjertman et al. | |
| 6,213,977 B1 | 4/2001 | Hjertman et al. | |
| 2001/0044606 A1 | 11/2001 | Inkpen et al. | |
| 2007/0118077 A1 | 5/2007 | Clarke et al. | |
| 2007/0225648 A1* | 9/2007 | Winsor et al. | 604/167.04 |

FOREIGN PATENT DOCUMENTS

| | | |
|---|---|---|
| JP | 9-10308 A | 1/1997 |
| JP | 2001-137343 A | 5/2001 |
| JP | 2009-516572 A | 4/2009 |

* cited by examiner

INJECTION NEEDLE ASSEMBLY AND DRUG INJECTION DEVICE

CROSS REFERENCE TO RELATED APPLICATIONS

This application is a National Stage of International Application No. PCT/JP2011/054852, filed on Mar. 3, 2011, which claims priority from Japanese Patent Application No. 2010-077107, filed on Mar. 30, 2011, the contents of all of which are incorporated herein by reference in their entirety.

TECHNICAL FIELD

This invention relates to an injection needle assembly and drug injection device, which are used to cause a needle tip to be punctured from a skin surface so as to inject a drug into the upper layer of skin.

BACKGROUND ART

In recent years, avian influenza infection in humans has been reported with concern that much damage is caused by infectious human-to-human pandemic outbreak. Therefore, there have been being built, in the world, stockpiles of a pandemic vaccine that would have the high possibility of being effective against the avian influenza. In order to administer the pandemic vaccine to many people, studies have been made on the increasing amount of production of the vaccine.

The skin is made up of three layers including the epidermis, the dermis and the subcutis. The epidermis is a layer of about 50 to 200 μm from the skin surface, and the dermis is a layer of about 1.5 to 3.5 mm contiguous to the epidermis. Generally, an influenza vaccine is subcutaneously or intramuscularly administered, for which it is administered in the lower section of the skin or in a deeper section.

On the other hand, it has been reported that when an influenza vaccine is administered in the upper layer of skin, as a target site, wherein immunocompetent cells exist abundantly, there can be obtained the capability of immune acquisition equal to that attained by subcutaneous or intramuscular administration if the amount of administration is reduced (Non-Patent Document 1). Accordingly, since the amount of administration can be reduced by administration of a pre-pandemic vaccine in the upper layer of skin, the amount of administration can be reduced and thus, the pre-pandemic vaccine can be administered to a greater number of people. It will be noted that the upper layer of skin indicates the epidermis and dermis of the skin.

For the administration of a drug in the upper layer of skin, there have been reported a number of methods making use of a single needle, a multistylus, a patch, a gas and the like. It has been accepted that when taking into account the stability and reliability of administration and the production cost, the method using a single needle is most suited as a method of administration in the upper layer of skin. For the method of administering a vaccine in the upper layer of skin by use of a single needle, the Mantoux method is known from long ago. The Mantoux method is one wherein a needle having a size of 26 to 27 gauge and a short bevel needle tip is generally inserted to a depth of about 2 to 5 mm from an inclined direction of about 0 to 15° relative to the skin so as to administer about 100 μl of a drug.

The administration procedure of a drug based on the Mantoux method is difficult, with its success rate being entrusted to the skill of a doctor who makes an injection. Especially, children are apt to act up upon administration and thus, it has been difficult to administer an influenza vaccine according to the Mantoux method. Hence, there has been demanded the development of a device, with which a vaccine can be simply administered in the upper layer of skin.

In Patent Document 1, there is described an injection device wherein a limiter having a skin contact surface is connected to a hub of a syringe. The limiter of the injection device set out in this Patent Document 1 is tubularly formed to cover around a needle tube and has a skin contact surface from which an injection needle projects. With this limiter, the length of the injection needle projecting from the skin contact surface (projection length) is regulated at 0.5 to 3.0 mm, under which a drug injected from the injection needle is administered in the skin.

PRIOR ART DOCUMENTS

Patent Document

Patent Document 1: Japanese Patent Laid-Open No. 2001-137343

Non-Patent Document

Non-Patent Document 1: R. T. Kenny et al. New England Journal of Medicine, 351, p. 2295-2301 (2004)

SUMMARY OF INVENTION

Problem to be Solved by the Invention

However, with an injection device having a relatively short projection length of a needle tube like the injection device described in Patent Document 1, when the syringe is slowly pressed against the skin or is pressed with a weak force, the needle tip of the needle tube has not been punctured in the skin or has been difficult to puncture. In addition, there is a problem that it has been difficult for a user to recognize the degree of a depressing force, at which the needle tube is punctured in a living body. As a consequence, not only there occurs a variation in depressing force of puncturing the needle, but also the needle tip of the needle tube does not arrives at a desired position, so that it has been difficult to reliably administer a drug in the upper layer of skin.

An object of the invention is to provide a injection needle assembly and drug injection device wherein while the above problems are taken into consideration, a depressing force and puncturing speed required when a needle tube is punctured in the skin can be ensured and a needle tip of the needle tube can be situated reliably in the upper layer of skin.

Means for Solving Problem

In order to solve the above problems and achieve the object of the invention, the injection needle assembly of the invention includes: a needle tube having a needle tip capable of being punctured in a living body; a hub holding the needle tube; and an adjustment section provided around the needle tube, having a needle projection surface from which the needle tip of the needle tube projects. The assembly further includes a stabilizing section extending from the hub and disposed to surround the needle tube, the stabilizing section having an end face that contacts with the skin when the needle tube is punctured in the living body. Moreover, there is also provided a puncture speed securing member that is movable along an axial direction of the needle tube and is disposed at the adjustment section or stabilizing section, the puncture speed securing member contacting the skin ahead of the needle tip of the needle tube at the time when the needle tube is punctured in the living body, for ensuring a speed and depressing force when the needle tube is punctured in the living body.

The drug injection device of the invention includes: a needle tube having a needle tip capable of being punctured in a living body; a hub holding the needle tube; an adjustment section disposed around the needle tube and having a needle projection surface from which a needle tip of the needle tube projects; and a syringe connected to the hub. There is also provided a stabilizing section extending from the hub and disposed to surround the needle tube, the stabilizing section having an end face that contacts with the skin when the needle tube is punctured in the living body. The device is characterized by further including a puncture speed securing member that is disposed at the adjustment section or stabilizing section movably in an axial direction of the needle tube, the puncture speed securing member contacting the skin ahead of the needle tip of the needle tube when the needle tube is punctured in the living body, for ensuring a speed and depressing force when the needle tube is punctured in the living body.

Effect of the Invention

According to the injection needle assembly and drug injection device of the invention, when the needle tube is punctured in the living body, its speed and depressing force can be transiently ensured by the action of the puncture speed securing member, so that the needle tip of the needle tube can be punctured swiftly in the living body. Consequently, even if the needle tube projects only a little distance from the adjustment section, the needle tip of the needle tube can be reliably punctured in a desired site of the upper layer of skin.

MODE FOR CARRYING OUT THE INVENTION

Figure 1:
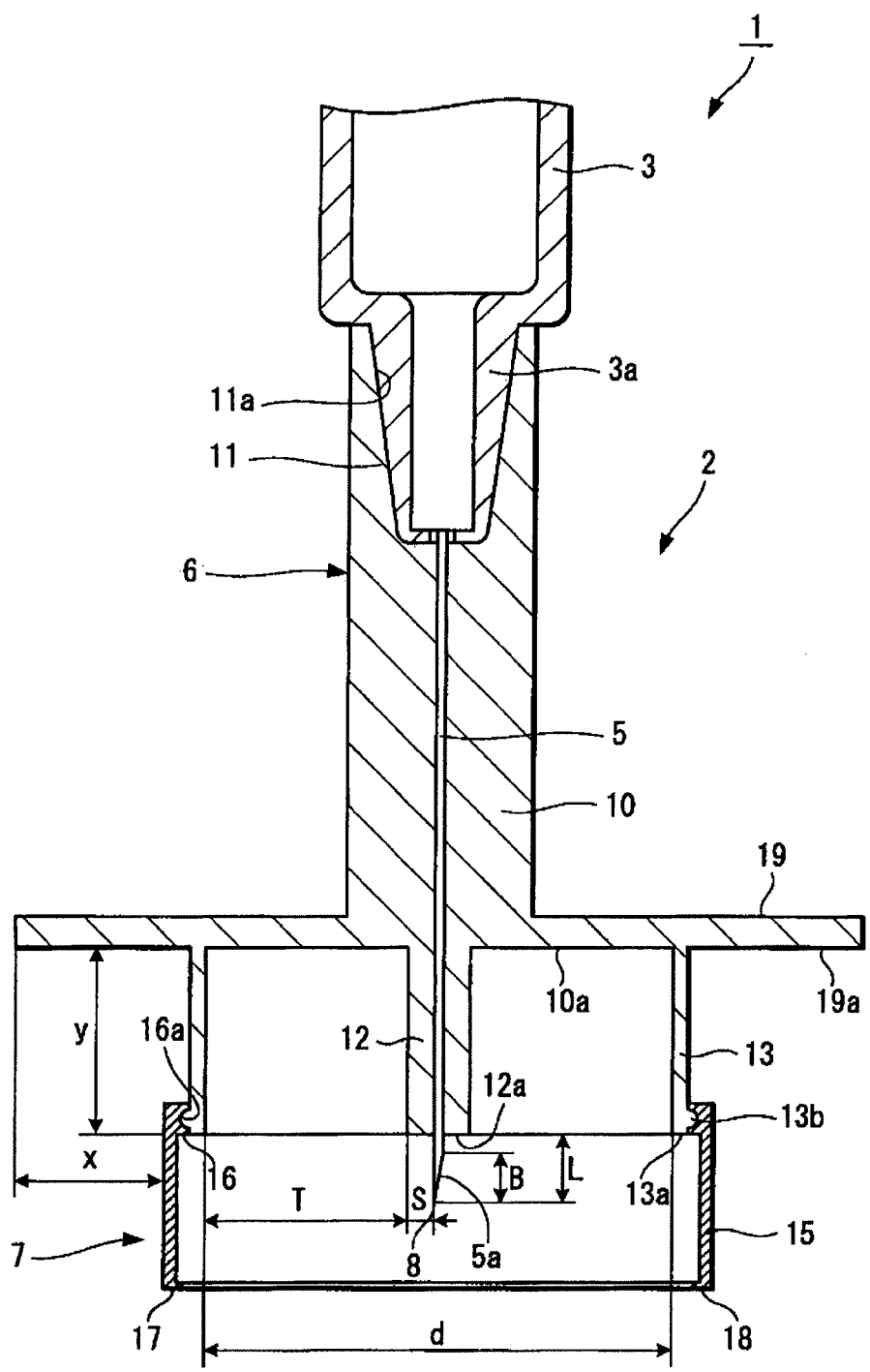
FIG. 1 is a sectional view showing a first embodiment of a drug injection device of the invention.

Embodiments of an injection needle assembly and drug injection device of the invention are now described with reference to FIGS. 1 to 6. It will be noted that like members are indicated by like reference numerals throughout the drawings. The invention should not be construed as limited to these embodiments.

Illustration is made in the following order.
1. First embodiment
   1-1. Configuration examples of injection needle assembly and drug injection device
   1-2. Manner of use of drug injection device
2. Second embodiment
3. Third embodiment <1. First Embodiment>
1-1. Configuration Examples of Injection Needle Assembly and Drug Injection Device Initially, an injection needle assembly and drug injection device according to a first embodiment (hereinafter referred to as "this embodiment") of the invention are described with reference to FIGS. 1 to 2.

Figure 2:
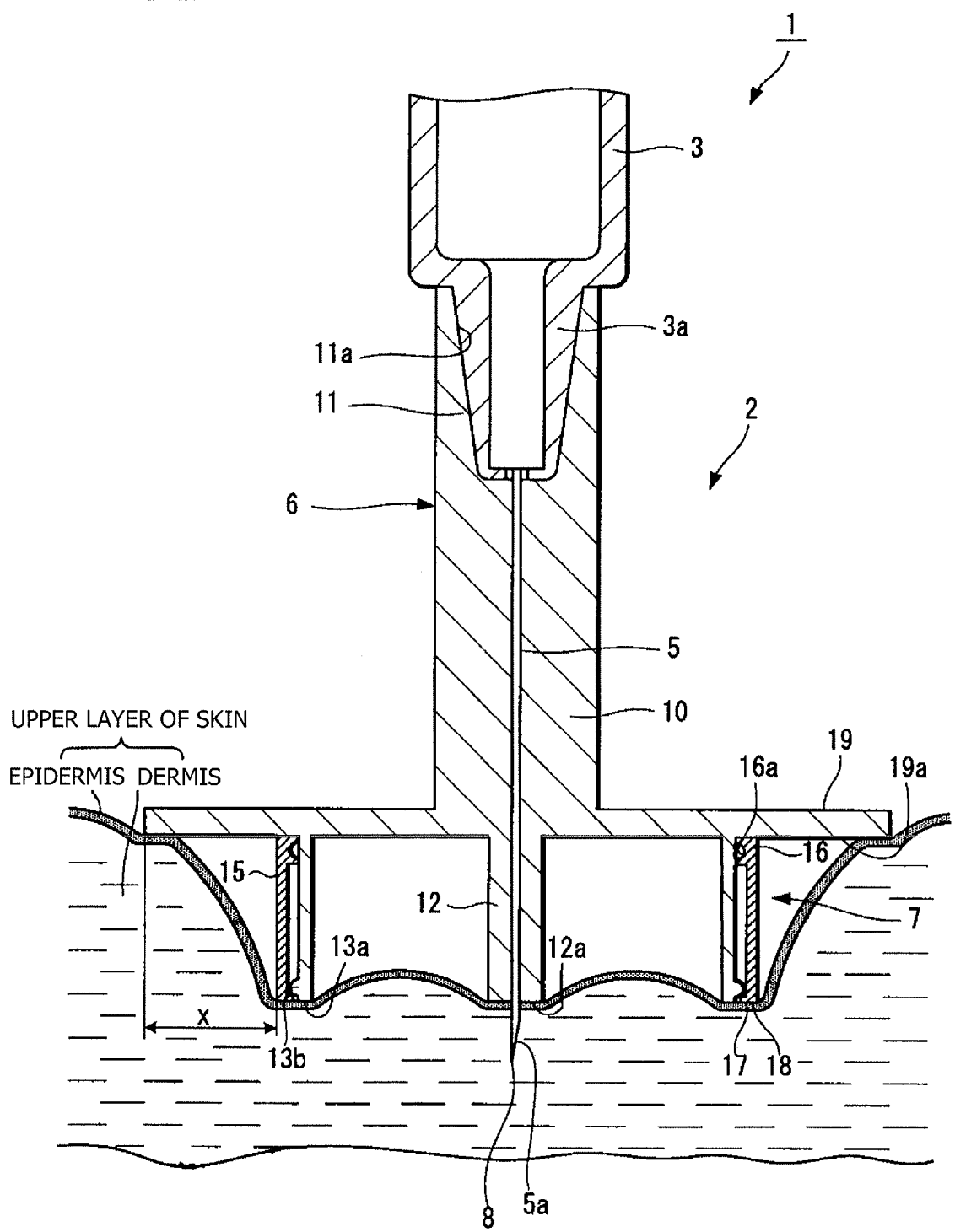
FIG. 2 is a sectional view showing a state of puncture in the first embodiment of the drug injection device of the invention.

FIG. 1 is a sectional view showing a drug injection device of this embodiment, and FIG. 2 is a section view showing a state where the device is punctured.

As shown in FIG. 1, a drug injection device 1 is composed of an injection needle assembly 2, and a syringe 3 to which the injection needle assembly 2 is detachably connected. The syringe 3 may be either one wherein a drug is filled at the time when the drug injection device is used or a pre-filled syringe having a drug filled beforehand. As a drug to be filled in the syringe 3, mention is made of vaccines. High molecular substances such as cytokine, and hormones may also be used.

The injection needle assembly 2 includes a hollow needle tube 5 having a needle hole, a hub 6 holding the needle tube 5, and a puncture speed securing member 7.

[Needle Tube]

The needle tube 5 used is one that has a size of 26 to 33 gauge (outer diameter: 0.2 to 0.45 mm), preferably 30 to 33 gauge, based on the ISO standards for medical needle tube (ISO 9626: 1991/Amd. 1: 2001 (E)). The needle tube 5 is formed at one tip end thereof with a blade face 5a so that a needle tip 8 is made acute-angled. The length of the blade face 5a (hereinafter referred to as "bevel length B") along the extending direction of the needle tube 5 may be not larger than 1.4 mm (adult) that is a smallest thickness of the upper layer of skin described hereinafter and not less than about 0.5 mm that is a bevel length when a short bevel is formed in the 33-gauge needle tube. That is, the bevel length B is preferably set within a range of 0.5 to 1.4 mm.

Further, the bevel length B is more preferably not larger than 0.9 mm (child) that is a smallest thickness of the upper layer of skin, i.e. a more preferred bevel length B is within a range of 0.5 to 0.9 mm. It should be noted that the short bevel means a blade face that is ordinarily employed in injection needles and is made at 18 to 25° relative to the lengthwise direction of the needle.

The materials for the needle tube 5 include, for example, stainless steels although not limited thereto. Other types of metals including aluminum, aluminum alloys, titanium and titanium alloys may also be used. As the needle tube 5, there may be used a straight needle and a tapered needle at least a part of which is tapered.

[Hub]

Next, the needle hub 6 is described. The hub 6 includes a hub body 10 having an approximately cylindrical shape, a fixing section 11, an adjustment section 12 and a stabilizing section 13. The hub body 10 is provided with the adjustment section 12 and the stabilizing section 13 at one end portion along the axial direction thereof and also with the fixing section 11 at the other end portion. The materials for the hub 6 include synthetic resins (plastics) such as polycarbonates, polypropylene, polyethylene and the like.

The fixing section 11 has a tubular hole 110, in which a fitting portion 3a of the syringe 3 is fitted. The tubular hole 11a is so set in size as to correspond to the fitting portion 3a of the syringe 3 and its diameter continuously decreases toward the side of the adjustment section 12 and the stabilizing section 13. It should be noted that the fixing section 11 may be formed at the inner peripheral surface thereof with a thread groove for screwing by fitting the fitting portion 3a of the syringe 3.

The adjustment section 12 is provided at the center of the end face 10a of the hub body 10 and is made up of a convex portion projecting in the axial direction of the hub body 10. An axis of the adjustment section 12 is coincident with an axis of the hub body 10. The needle tube 5 is passed through the adjustment section 12 and the hub body 10, and the axes of the needle tube 5 and the adjustment section 12 coincide with each other. The end face of the adjustment section 12 becomes a needle projection surface 12a that projects the needle tip 8 side of the needle tube 5.

The needle projection surface 12a is formed as a plane surface axially intersecting at right angles with the needle tube 5. When the needle tube 5 is punctured in the upper layer of skin, this needle projection surface 12a contacts the skin surface and regulates a puncture depth of the needle tube 5. More particularly, the puncture depth of the needle tube 5 in the upper layer of skin is determined by a length of the needle tube 5 (hereinafter referred to as "projection length L") projecting from the needle projection surface 12a.

The thickness of the upper layer of skin corresponds to a depth of from the skin surface to the dermic layer and is generally within a range of 0.5 to 3.0 mm. Accordingly, the projection length L of the needle tube 5 can be set within a range of 0.5 to 3.0 mm.

By the way, a vaccine is usually administered to the brachial region. When considering the administration to the upper layer of skin, it is considered proper to administer it to a region around the shoulder, particularly, the deltoid region, at which the skin is thick. Nineteen children and 31 adults were subjected to measurement of the thickness of the upper layer of skin of the deltoid muscles. This measurement was made by use of a ultrasonic measuring device (NP60R-UBM, high-resolution echo imaging device for small animals, Nepa Gene Co., Ltd.) for imaging the upper layer of skin whose ultrasonic reflectivity is high. It should be noted that the measurements had a normal distribution and a range of MEAN±2SD was thus determined by geometric average.

As a result, the thickness of the upper layer of skin in the deltoid muscles of the children was found to be at 0.9 to 1.6 mm. The thickness of the upper layer of skin in the deltoid muscles of the adults was found to be at 1.4 to 2.6 mm for the distal portion, at 1.4 to 2.5 mm for the central portion and at 1.5 to 2.5 mm for the proximal portion. In view of the above, it was confirmed that the thickness of the upper layer of skin in the deltoid muscles was at not less than 0.9 mm for children and at not less than 1.4 mm for adults. Accordingly, for the injection into the upper layer of skin of the deltoid muscles, it is preferred to set the projection length L of the needle tube 5 within a range of 0.9 to 1.4 mm.

When the projection length L is so set as defined above, it becomes possible to reliably situate the blade face 5a of the needle tip 8 at the upper layer of skin. Consequently, if the needle hole (drug discharge port) opened at the blade face 5a is positioned at any portion of the blade face 5a, it can be arrived to the upper layer of skin. It will be noted that even if the drug discharge port is located in the upper layer of skin, the needle tip 8, punctured too deeply in the upper layer of skin, causes a drug to be seeped under a subcutaneous portion from a space between the side face of the end portion of the needle tip 8 and the cut skin. To avoid this, it is important that the blade face 5a be reliably located in the upper layer of skin.

It will be noted that with a needle tube that is thicker than 26 gauge, it is difficult to make the bevel length B at not larger than 1.0 mm. Accordingly, in order to set the projection length L of the needle tube 5 within the preferred range (of 0.9 to 1.4 mm), the use of a needle tube that is thinner than 26 gauge is preferred.

The needle projection surface 12a is so formed that a distance S of from the peripheral edge thereof to the peripheral surface of the needle tube 5 is at not larger than 1.4 mm, preferably within a range of 0.3 to 1.4 mm. The distance S of from the peripheral edge of the needle projection surface 12a to the peripheral surface of the needle tube 5 is set while taking it into consideration that a pressure is exerted on vesicles formed by administering a drug in the upper layer of skin. That is, the needle projection surface 12a is so set that it is much smaller than the vesicles formed in the upper layer of skin and has a size enough not to impede the formation of the vesicles. As a consequence, when the needle projection surface 12a presses the skin around the needle tube 5, leakage of a drug being administered can be prevented.

Next, the stabilizing section 13 is illustrated.

The stabilizing section 13 is provided at an end face 10a of the hub body 10. This stabilizing section 13 is tubularly formed contiguously to the peripheral edge portion of the end face 10a. The needle tube 5 and the adjustment section 12 are arranged in the tubular hole of the stabilizing section 13. That is, the stabilizing section 13 is tubularly formed to surround the adjustment section 12, through which the needle tube 5 is inserted. An end face 13a of the stabilizing section 13 is situated substantially on the same plane surface as the needle projection surface 12a of the adjustment section 12.

When the needle tip 8 of the needle tube 5 is punctured in a living body, the needle projection surface 12a contacts the skin surface and also contacts the end face 13a of the stabilizing section 13. At this time, since the end face 13a of the stabilizing section 13 contacts the skin, the drug injection device 1 is stabilized and the needle tube 5 can be held in a posture substantially vertical to the skin.

It will be noted that if the end face 13a of the stabilizing section 13 is situated on the same plain surface as the needle projection surface 12a or is situated nearer to the needle tip 8 side of the needle tube 5 than the needle projection surface 12a, the needle tube 5 can be kept in a posture substantially vertical to the skin. It will also be noted that when the elevation of the skin is taken into account under pressing of the stabilizing section 13 against the skin, it is preferred that the distance in an axial direction between the end face 13a of the stabilizing section 13 and the needle projection surface 12a is set at not larger than 1.3 mm.

Furthermore, the inner diameter d of the stabilizing section 13 is set equal to or larger than the diameter of vesicles formed in the skin. More particularly, a distance T of from the inner wall surface of the stabilizing section 13 to the peripheral edge of the needle projection surface 12a is set within a range of 4 mm to 15 mm. This can prevent vesicle formation from being inhibited due to the application of a pressure to the vesicles from the inner wall surface of the stabilizing section 13.

The distance T of from the inner wall surface of the stabilizing section 13 to the peripheral edge of the needle projection surface 12a has no upper limit so far as it is at not less than 4 mm. However, a larger distance T results in a larger outer diameter of the stabilizing section 13. Accordingly, where a slender arm such as of a child is punctured with the needle tube 5, it becomes difficult to bring the entire end face 13a of the stabilizing section 13 into contact with the skin. In this sense, it is preferred to regulate the distance T at 15 mm in maximum while taking the slenderness of child's arm into account.

If the distance S of from the peripheral edge of the needle projection surface 12a to the peripheral surface of the needle tube 5 is at not less than 0.3 mm, the adjustment section 12 does not enter into the skin. Accordingly, when taking the distance T (not less than 4 mm) of from the inner wall surface of the stabilizing section 13 to the peripheral edge of the needle projection surface 12a and the diameter (about 0.3 mm) of the needle projection surface 12a into consideration, the inner diameter d of the stabilizing section 13 can be set at not less than 9 mm.

It will be noted that the shape of the stabilizing section 13 is not limited to the cylinder, but may be, for example, in a horn-shaped form, such as a quadratic prism, a hexagonal column or the like, having a tubular hole at the center thereof.

Further, the stabilizing section 13 has a guide portion 19 serving as a depressing indicator. The guide portion 19 is continuously provided along the periphery of the outer peripheral surface of the stabilizing section 13 and is formed as a ring-shaped flange projecting in a radial outer direction of the stabilizing section 13. This guide portion 19 has a contact face 19a contacting the skin. The contact face 19a is on the same plane surface substantially parallel to the end face 13a of the stabilizing section 13.

When the stabilizing section 13 is depressed until the contact face 19a of the guide portion 19 contacts the skin, a force of depressing the skin with the stabilizing section 13 and the needle tube 5 can be invariably held at not less than a given value. In this way, the portion projecting from the needle projection surface 12a of the needle tube 5 (corresponding to the projection length L) can be reliably punctured in the skin.

A distance of from the contact face 19a of the guide portion 19 to the end face 13a of the stabilizing section 13 is so set in length that the stabilizing section 13 and the needle tube 5 can be punctured in the skin by an appropriate depressing force (see FIG. 2). This length is hereinafter referred to as "guide portion height y."

It will be noted that an appropriate depressing force of the needle tube 5 and the stabilizing section 13 is, for example, at 0.5 to 20 N. As a result, a user is allowed to be guided with the guide portion 19 with respect to the pressing force of the needle tube 5 and the stabilizing section 13 against the skin, and the needle tip 8 and the blade face 5a of the needle tube 5 can be reliably situated in the upper layer of skin, so that such an effect of giving a sense of safety to the user can be obtained.

In particular, the inner diameter d of the stabilizing section 13 is preferably within a range of 11 to 14 mm, and the guide portion height y is appropriately determined based on a length x of from the projection end face of the guide portion 19 to an outer peripheral surface of a ring body 15 of a puncture speed securing member 7 described hereinafter (see FIG. 2 and hereinafter referred as guide portion length x). For instance, if the inner diameter d of the stabilizing section 13 is at 12 mm and the guide portion length x is, for example, at 3 mm, the guide portion height y is set within a range of 2.3 to 6.6 mm. Additionally, the total of the thickness of the ring body 15 and the thickness of the stabilizing section 13 is preferably at not larger than generally 2 mm.

A portion 13b to be engaged is provided on the outer peripheral surface at the side of the end face 13a of the stabilizing section 13. The portion 13b to be engaged is continuously formed along the peripheral direction of the outer peripheral surface of the stabilizing section 13. The portion 13b to be engaged is a protrusion which projects substantially semicircularly in section from the outer peripheral surface of the stabilizing section 13. This portion 13b to be engaged is engaged with a puncture speed securing member 7 described hereinafter. In addition, the stabilizing section 13 is slidably attached with the puncture speed securing member 7 along an axial direction thereof.

[Puncture Speed Securing Member]

Next, the puncture speed securing member 7 is described. The puncture speed securing member 7 has the ring body 15 formed in ring form and an engaging portion 16 provided at the ring body 15. The ring body 15 has an inner diameter that is larger than the diameter (outer diameter) of the stabilizing section 13. This ring body 15 is slidably attached to the outer peripheral surface of the stabilizing section 13 in an axial direction thereof.

The engaging portion 16 is disposed on an inner peripheral surface at one end portion in the axial direction of the ring body 15. The engaging portion 16 projects toward the radial inner direction from the inner peripheral surface of the ring body 15. At a projection tip end of the engaging portion 16, there is formed a groove portion 16a engaging with the portion 13b to be engaged and recessed substantially in semicircular form in section. This groove portion 16a is formed continuously along the peripheral direction of the inner peripheral surface of the ring body 15.

When a depressing force exceeding a given force is put thereon, the engaging portion 16 and the portion 13b to be engaged are disengaged. In this instance, the depressing force permitting the disengagement between the engaging portion 16 and the portion 13b to be engaged is set, for example, within a range of 3 to 20 N.

It will be noted that although the continuous formation of the groove portion 16a along the peripheral direction of the inner peripheral surface of the ring body 15 has been set out in this instance, the invention is not limited thereto. For instance, the groove portion 16a may be formed discontinuously on the inner peripheral surface of the ring body 15. In this case, the portion 13b to be engaged of the stabilizing section 13 is formed discontinuously on the outer peripheral surface of the stabilizing section 13 correspondingly to the groove portion 16a of the engaging portion 16.

Furthermore, the sectional shape of the portion 13b to be engaged is not limited to be substantially semicircular, but may be formed in a substantially triangular or substantially quadrangular shape. More particularly, as to the sectional shape of the portion 13b to be engaged, its purpose can be achieved if there is used such a shape that allows disengagement with the engaging portion 16 by application of a given depressing force. The groove portion 16a of the engaging portion 16 is formed in a shape corresponding to the sectional form of the portion 13b to be engaged.

An inner flange portion 17 projecting toward the radial inner direction of the ring body 15 is provided at an end portion opposite to the end portion, at which the engaging portion 16 in the ring body 15 is provided. As shown in FIG. 2, the inner flange portion 17 comes in abutment with the portion 13b to be engaged of the stabilizing section 13 after disengagement with the engaging portion 16.

Further, the end face at the side where the inner flange portion 17 in the ring body 15 is formed serves as an abutment face 18 that initially contacts a living body when the needle tube 5 is punctured in the living body. More particularly, in a state prior to the puncture of the needle tube 5 in the living body, the ring body 15 is situated at a first position covering the needle tip 8 of the needle tube 5 and part of the adjustment section 12. That is, the abutment face 18 projects toward the skin side rather than the needle tip 8 of the needle tube 5 and the end face 13a of the stabilizing section 13.

As will be described hereinafter, when the hub 6 or syringe 3 is held and the abutment face 18 of the ring body 15 abuts the skin to push out the hub 6 toward the skin side, the engagement between the engaging portion 16 and the portion 13b to be engaged is released. The ring body 15 is slidingly moved along the outer peripheral surface of the stabilizing section 13 in the axial direction of the hub 6. Consequently, the ring body 15 allows the needle tip 8 of the needle tube 5 to be exposed, and the abutment face 18 is moved to a second position situated substantially on the same plane surface as the end face 13a of the stabilizing section 13.

It will be noted that the shape of the stabilizing section 13 is not limited to the cylindrical form, but may be in a horn-shaped form, such as a quadratic prism, a hexagonal column or the like, having a tubular hole at the center thereof. The shape of the ring body 15 of the puncture speed securing member 7 is determined correspondingly to the shape of the stabilizing section 13.

Although the instance of arranging the ring body 15 at the outer peripheral surface side of the stabilizing section 13 has been described in this embodiment, the invention is not limited thereto, and the ring body 15 may be set at the inner peripheral surface side of the stabilizing section 13. Where the ring body 15 is set at the inner peripheral surface side of the stabilizing section 13, the portion 13b to be engaged is disposed on the inner peripheral surface of the stabilizing section 13 and the engaging portion 16 is disposed on the outer peripheral surface of the ring body 15.

Where the ring body 15 is set at the inner peripheral surface side of the stabilizing section 13, it is preferred that the inner diameter of the ring body 15 is set equal to or larger than the diameter of vesicles formed in the skin. More particularly, the shortest distance of from the inner wall surface of the ring body 15 to the outer peripheral surface of the adjustment section 12 is set within a range of 4 mm to 15 mm. The guide portion length x is set at a distance of from the projection end face of the guide portion 19 to the outer peripheral surface of the stabilizing section 13.

Although such an instance that the guide portion 19 is disposed at the stabilizing section 13 has been illustrated above, the guide portion 19 may be provided on the outer peripheral surface of the ring body 15 of the puncture speed securing member 7.

1-2. Manner of Use of the Drug Injection Device

Next, how to use the drug injection device 1 of this embodiment is illustrated with reference to FIGS. 1 to 2.

Initially, the abutment face 18 of the ring body 15 of the puncture speed securing member 7 is set oppose to the skin. This permits the needle tip 8 of the needle tube to come face-to-face with the skin to be punctured. It is to be noted that as shown in FIG. 1, the ring body 15 is situated at the first position and the abutment face 18 projects from the hub 6 toward the skin side further than the needle tip 8 of the needle tube 5. More particularly, the needle tip 8 of the needle tube 5 and the side surface of the stabilizing section 13 are covered with the ring body 15.

Next, the injection needle assembly 2 is moved substantially vertically to the skin to press the abutment face 18 of the ring body 15 against the skin. At this stage, because the engaging portion 16 and the portion 13b to be engaged are engaged with each other, the ring body 15 is situated at the first position until the engagement between the engaging portion 16 and the portion 13b to be engaged is released.

As shown in FIG. 2, when the injection needle assembly 2 is pressed against the skin by a force that is greater than the engaging force between the engaging portion 16 and the portion 13b to be engaged, the engagement between the engaging portion 16 and the portion 13b to be engaged is released. Since the engagement between the engaging portion 16 and the portion 13b to be engaged is released, the hub 6 loses the resistance force from the engaging portion 16. This causes the ring body 15 to be slidingly moved abruptly along the outer peripheral surface of the stabilizing section 13 in the axial direction thereof, so that the needle tip 8 of the needle tube 5 is rushed out from the opening of the ring body 15.

In this way, when the engaging portion 16 of the puncture speed securing member 7 and the portion 13b to be engaged of the stabilizing section 13 are engaged and this engagement is released, the depressing force and puncturing speed can be transiently increased. As a consequence, the needle tip 8 of the needle tube 5 can be reliably punctured in the skin, and puncture to the upper layer of skin is enabled.

Upon disengagement between the engaging portion 16 and the portion 13b to be engaged, a sense of click is felt, so that it is delivered to a user that the depressing force and speed for puncturing the needle tube 5 in the living body increase. This enables the user to confirm that the injection needle assembly 2 can be pressed at a proper depressing pressure, so that there can be obtained an effect of imparting a sense of safety to the user.

Further, the skin can be deformed flatly by contact of the needle projection surface 12a of the adjustment section 12 with the skin and thus, the needle tube 5 can be punctured in the skin only by the projection length L.

Next, the stabilizing section 13 is pressed until the contact surface 19a of the guide portion 19 is brought into contact with the skin. As to the guide portion height y, its length is so set that the needle tube 5 and the stabilizing section 13 can be punctured in the skin at a proper depressing force. Accordingly, the force of depressing the skin with the hub 6 becomes a given value. In doing so, when a drug is injected, the needle tip 8 is held in the upper layer of skin, so that no leakage of the drug takes place and it becomes possible to inhibit the drug from arriving under a subcutaneous portion.

In this manner, with the aid of the sense of click created by means of the puncture speed securing member 7 and the guide portion 19 serving as an indicator of guiding the depressing force of the hub 6, a user can be informed of a depressing force necessary for the puncture of the needle tube 5 in a living body and also for the injection of a drug, respectively. Thus, a sense of safety can be imparted to the user.

When the stabilizing section 13 and the ring body 15 comes in abutment with the skin, the needle tube 5 is stabilized and the needle tube 5 can be punctured and held vertically to the skin. Thus, a variation involved in the needle tube 5 can be prevented and stable administration of a drug can be made.

With a needle whose projection length is, for example, as very short as about 0.5 mm, there may be some case that the needle tip 8 is not punctured in the skin if brought into abutment with the skin. In this connection, however, the puncture speed is so fast that skin incision with the needle tip 8 readily occurs. Moreover, when the stabilizing section 13 and the ring body 15 are pressed against the skin to hold down the skin in the vertical direction, the skin at the inner side of the stabilizing section 13 is pulled to create a state of the skin being under tension. This makes it difficult to allow the skin to escape relative to the needle tip 8 of the needle tube 5, with the attendant effect of the stabilizing section 13 that the needle tip 8 is more likely to be punctured in the skin.

Further, since the projection length L is set within a range of 0.5 to 3.0 mm, the needle tip 8 and the blade face 5a of the needle tube 5 are reliably situated within the upper layer of skin. Thereafter, a drug is injected into the upper layer of skin by means of the syringe 3 connected to the hub 6.

The adjustment section 12 of the injection needle assembly 2 is in intimate contact with and is fixed to the periphery of the needle tube 5 in such a way that no space is formed between the portion passing through the adjustment section 12 of the needle tube 5 and the adjustment section 12. Hence, when the needle projection surface 12a of the adjustment section 12 is brought into abutment with the skin, the skin around the needle tube 5 can be deformed flat. As a result, the needle tube 5 can be punctured in the skin only by the projection length L and the needle tip 8 of the needle tube 5 can be reliably situated within the upper layer of skin.

The needle projection surface 12a of the adjustment section 12 and the inner diameter d of the stabilizing section 13 are set properly in size, so that an injected drug can be inhibited from leaking to outside and thus, the drug can be reliably administered within the upper layer of skin.

<2. Second Embodiment>

Next, a second embodiment of a drug injection device of the invention is described with reference to FIGS. 3 and 4.

Figure 3:
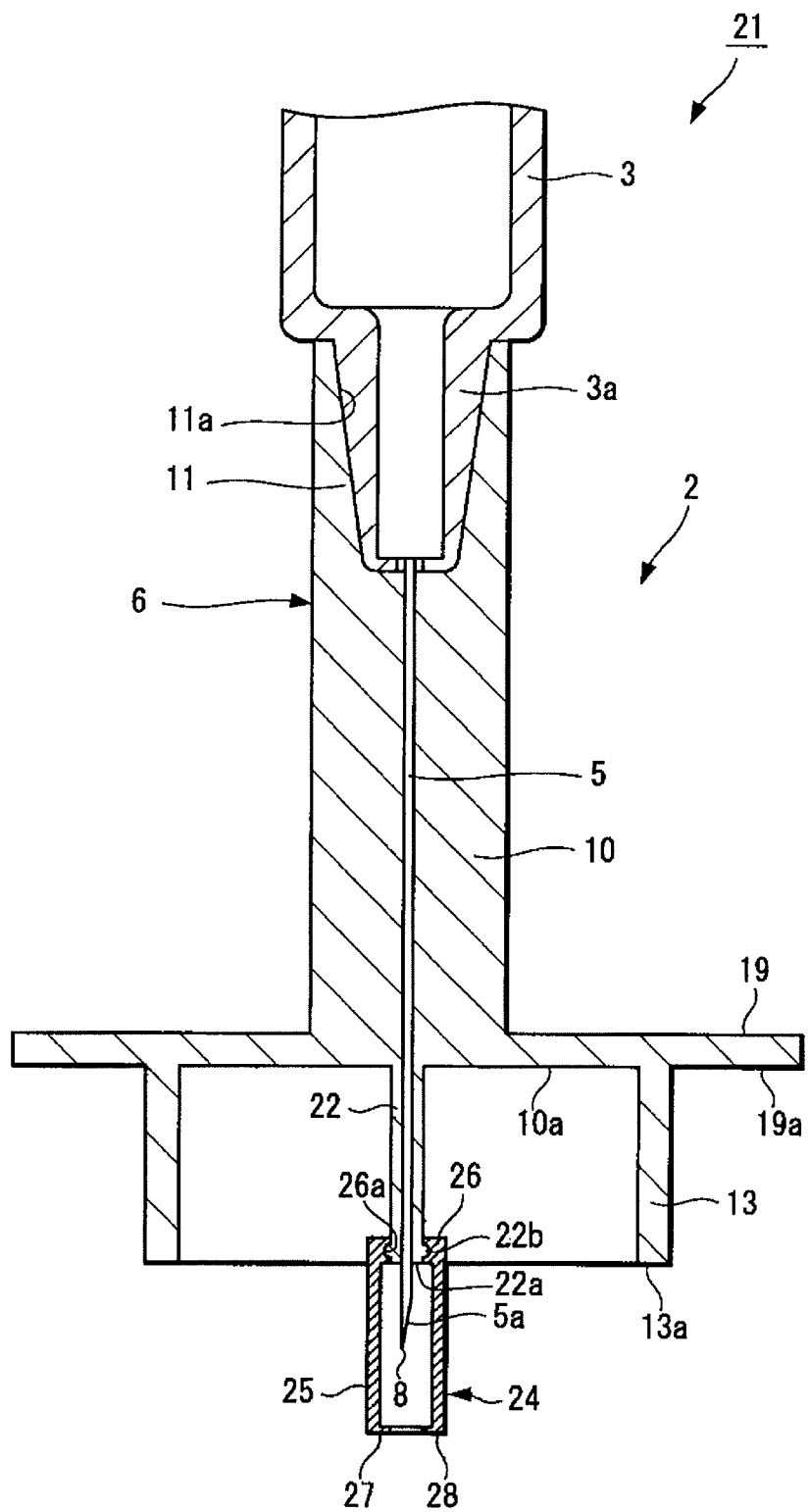
FIG. 3 is a sectional view showing a second embodiment of a drug invention device of the invention.
Figure 4:
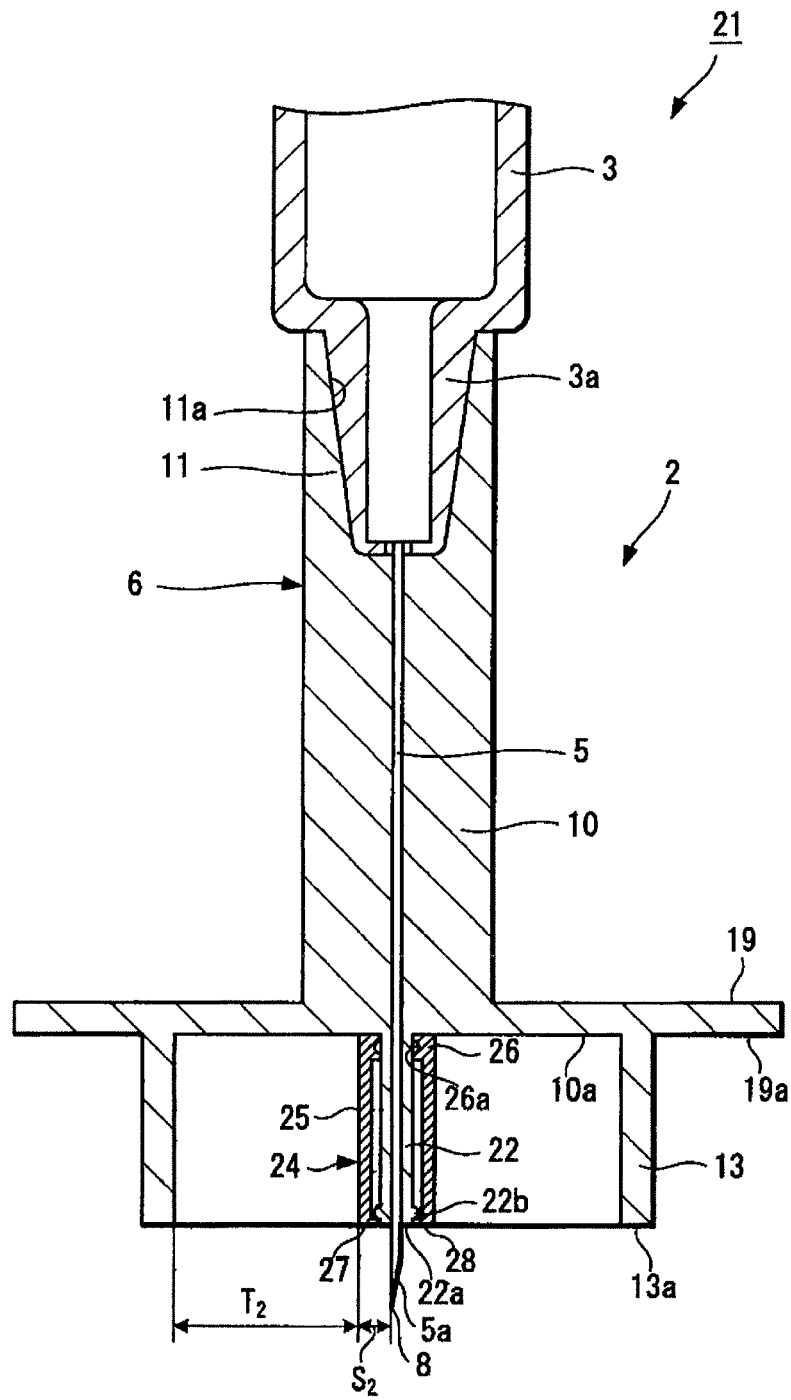
FIG. 4 is a sectional view showing a state after puncture in the second embodiment of the drug injection device of the invention.

FIGS. 3 and 4 are, respectively, a sectional view showing a drug injection device according to the second embodiment.

A drug injection device 21 related to the second embodiment differs from the drug injection device 1 of the first embodiment in that the puncture speed securing member is disposed at the adjustment section. The puncture speed securing member and adjustment section are described herein and like portions common with the drug injection device 1 are indicated by like reference numerals for avoiding redundancy.

As shown in FIG. 3, an adjustment section 22 is disposed at a central portion of one end face 10a of a hub body 10 and is configured as a substantially cylindrical protrusion portion projecting in an axial direction of the hub body 10. At an end portion of the adjustment section 22 at a side opposite to the hub body 10, a portion 22b to be engaged is provided. The portion 22b to be engaged projects continuously along the peripheral direction of the outer peripheral surface of the adjustment section 22 in a radial outer direction. The sectional shape of the portion 22b to be engaged is formed substantially semicircularly. A puncture speed securing member 24 is slidably attached to the adjustment section 22 in the axial direction.

The puncture speed securing member 24 has a ring-shaped ring body 25 and an engaging portion 26 disposed to the ring body 25. The ring body 25 has an inner diameter greater than the diameter of the ring body 22. This ring body 25 is slidably attached to the outer peripheral surface of the adjustment section 22 in its axial direction.

The engaging portion 26 is disposed on the inner peripheral surface at one end portion of the ring body 25 in the axial direction thereof. The engaging portion 16 projects toward the radial inner direction from the inner peripheral surface of the ring body 15. At the tip end of the projection of the engaging portion 26, there is formed a groove 26a which is recessed substantially semicircularly in section and engages the portion 22b to be engaged. This groove portion 26a is formed continuously along the peripheral direction of the inner peripheral surface of the ring body 15. When a depressing force not smaller than a given force is inputted, the engagement between the engaging portion 26 and the portion 22b to be engaged is released.

At an end portion opposite to the end portion disposed with the engaging portion 26 in the ring body 25, there is provided an inner flange portion 27 projecting toward the radial inner direction of the ring body 25.

As shown in FIG. 4, the inner flange portion 27 is in abutment with the portion 22b to be engaged of the adjustment section 22, which has been disengaged from the engaging portion 26.

Furthermore, an end face at a side where the inner flange portion 27 in the ring body 25 is formed becomes an abutment face 28 to be brought into contact with a living body when the needle tube 5 is punctured in the living body. In a state prior to the puncture of the needle tube 5 in a living body, the ring body 25 is situated at first position covering the needle tip 8 of the needle tube 5 and part of the adjustment section 22. More particularly, the abutment face 28 projects toward the skin side further than the needle tip 8 of the needle tube 5 and the end face 13a of the stabilizing section 13.

As shown in FIG. 4, when the ring body 25 is moved to a second position after disengagement between the engaging portion 26 and the portion 22b to be engaged, the abutment face 28 is situated substantially on the same plain surface as the end face 13a of the stabilizing section 13 and the needle projection surface 22a of the adjustment section 22.

Other configurations are similar to those of the drug injection device 1 according to the foregoing first embodiment and their illustration is omitted. According to the drug injection device 21 having such configurations as set out above, there can be obtained similar advantages and effects as with the case of the drug injection device 1 according to the first embodiment.

It will be noted that in order to prevent the formation of vesicles from being inhibited, a shortest distance $T_2$ of from the inner wall surface of the stabilizing section 13 to the outer peripheral surface of the ring body 25 of the puncture speed securing member 24 is set within a range of 4 mm to 15 mm (see FIG. 4). In doing so, the formation of vesicles can be prevented from being inhibited by application of a pressure to vesicles from the end face 13a of the stabilizing section 13 and the abutment face 28 of the ring body 25.

Further, in the state that the end face 13a of the stabilizing section 13 and the needle projection surface 22a of the adjustment section 22 are situated on the same plain surface as shown in FIG. 4, the distance $S_2$ of from the peripheral edge of the ring body 25 to the peripheral surface of the needle tube 5 is so determined that no pressure is exerted on the vesicles to be formed by administration of a drug in the upper layer of skin. More particularly, the needle projection surface 22a and the abutment face 28 of the ring body 25 are so set in size as to be appreciably smaller than the vesicles formed in the upper layer of skin so as not to inhibit the formation of the vesicles. As a result, an administered drug can be prevented from being leaked out caused by the skin around the needle tube 5 being depressed by the needle projection surface 22a and the abutment face 28.

<3. Third Embodiment>

Next, a third embodiment of a drug injection device of the invention is described with reference to FIGS. 5 and 6.

Figure 5:
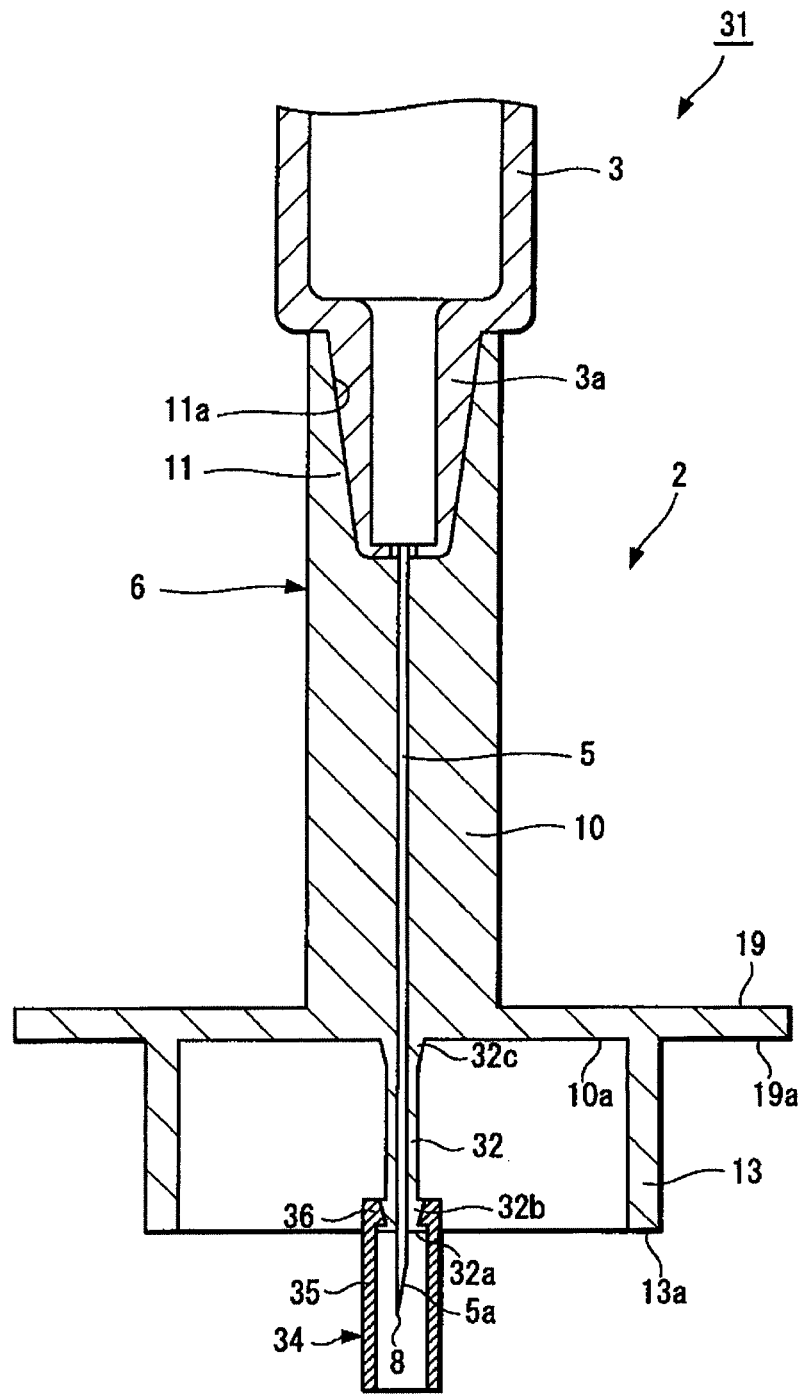
FIG. 5 is a sectional view showing a third embodiment of a drug injection device of the invention.
Figure 6:
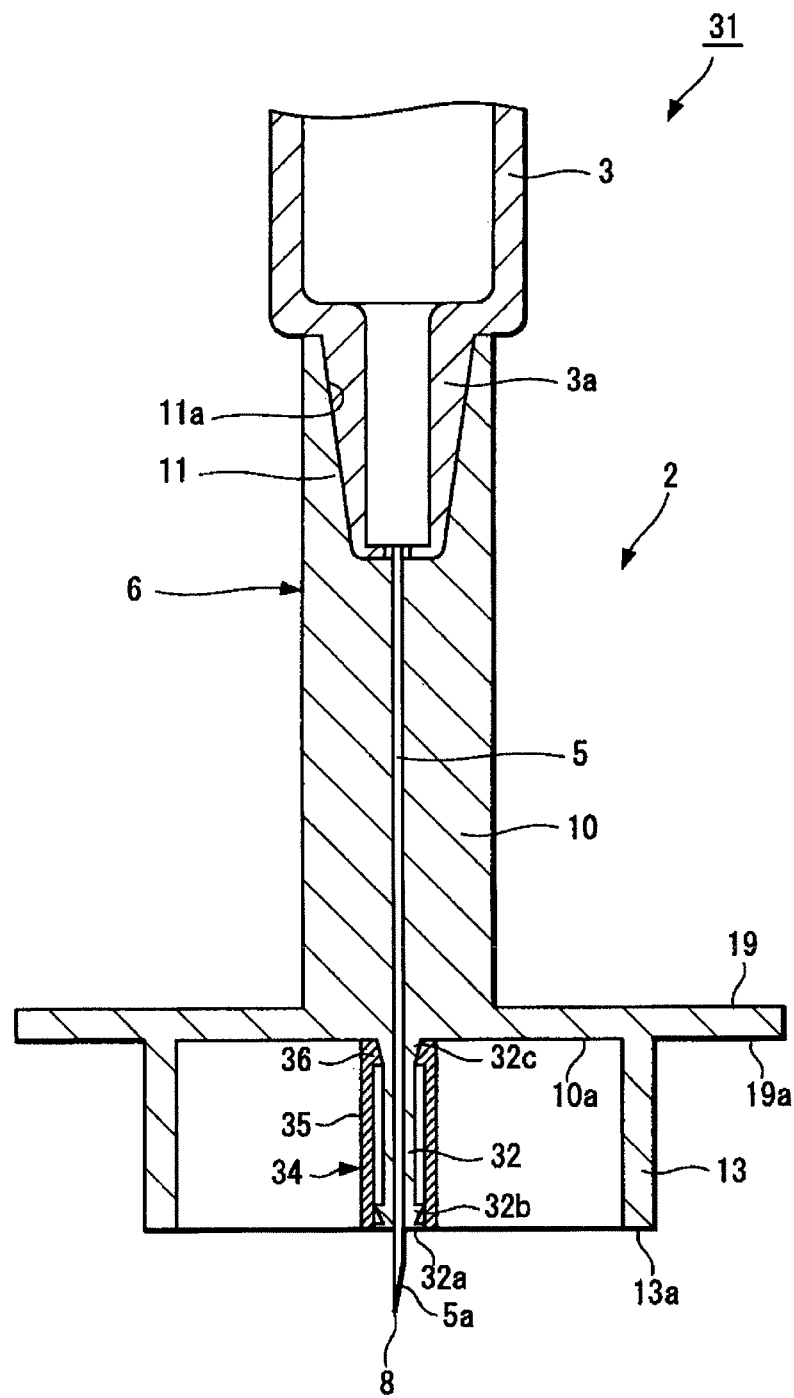
FIG. 6 is a sectional view showing a state after puncture in the third embodiment of the drug injection device of the invention.

FIGS. 5 and 6 are, respectively, a sectional view showing a drug injection device according to the third embodiment.

A drug injection device 31 according to the third embodiment includes a modified configuration of the puncture speed securing member and the adjustment section of the drug injection device 21 of the second embodiment. Hence, a puncture speed securing member and adjustment section are illustrated herein. Like portions common with the drug injection device 1 are indicated by like reference numerals for avoiding redundancy.

As shown in FIG. 5, an adjustment section 32 has a needle projection surface 32a, a portion 32b to be engaged and a portion 32c to be fitted. The needle projection surface 32a is an end face at an opposite side of a hub body 10 in the adjustment section 32, from which the needle tip 8 of the needle tube 5 projects.

The portion 32b to be engaged is disposed at an end portion of a side opposite to the hub body 10 in the adjustment section 32. The portion 32b to be engaged is a protrusion portion projecting from the outer peripheral surface of the adjustment section 32 substantially in triangular form in section. The portion 32c to be fitted is disposed at an end portion of a side of the hub body 10 in the adjustment section 32. The portion 32c to be fitted projects from the outer peripheral surface of the adjustment section 32 and the end face 10a of the hub body 10 and is formed in substantially triangular form in section. Moreover, in a region between the portion 32b to be engaged and the portion 32c to be fitted in the adjustment section 32, its diameter is set smaller than in the other portions. The adjustment section 32 is attached with a puncture speed securing member 34 that is slidably movable in an axial direction thereof.

The puncture speed securing member 34 has a ring body 35 formed in ring form, and an engaging portion 36 provided at the ring body 35. The inner diameter of the ring body 35 is set substantially equal to or slightly larger than the diameter of the needle projection surface 32a of the adjustment section 32. The inner peripheral surface of one end portion along an axial direction of the ring body 35 is provided with an engaging portion 36.

The engaging portion 36 projects from the inner peripheral surface of the ring body 35 toward the radial inner direction. This engaging portion 36 is formed substantially in triangular form in section. When the ring body 35 is situated at a first position, the engaging portion 36 is engaged with the portion 32b to be engaged of the adjustment section 32. As shown in FIG. 6, when the ring body 35 is moved to a second position, the engaging portion 36 is fitted with the portion 32c to be fitted of the adjustment section 32. In doing so, it can be regulated that the ring body 35 is returned from the second position to the first position.

Further, a site between the portion 32b to be engaged and the portion 32c to be fitted of the adjustment section 32 is formed to have a diameter smaller than other portions. Hence, when the ring body 35 slidingly moves on the adjustment section 32 after disengagement between the engaging portion 36 and the portion 32b to be engaged, the frictional resistance between the ring body 35 and the adjustment section 32 can be made small. Consequently, the depressing force and puncture speed, which have been secured upon disengagement between the engaging portion 36 and the portion 32b to be engaged, are prevented from being reduced owing to the frictional resistance between the ring body 35 and the adjustment section 32. Thus, a proper depressing force and puncture speed can be imparted to the stabilizing section 13 and the needle tube 5.

Other configurations are similar to those of the drug injection device 1 related to the afore-described first embodiment and the drug injection device 21 related to the second embodiment and are not illustrated herein again. According to the drug injection device 31 having such a configuration as stated above, there can be obtained operations and effects as with the drug injection device 1 according to the first embodiment.

It will be noted that the invention is not limited to the embodiments set forth above and shown in the drawings and may be variously altered without departing from the scope of the invention as recited in the claims. For instance, the puncture speed securing member may be slidingly moved to cover the outer side in the radial direction of the guide portion. It will be noted that in the foregoing embodiments, illustration has been made on the instance where the depressing indicator is formed in the form of a flange, but not limited thereto. For example, the depressing indicator may be formed by provision of a step by substantially vertically notching the outer peripheral surface of the stabilizing section.

Furthermore, in order to regulate that the ring body of the puncture speed securing member returns from the second position to the first position, a stopper portion may be provided at the hub and ring body so as to fix the ring body to the second position. Moreover, the engaging portion side is provided as a groove portion and the side of the portion to be engaged is provided as a protrusion portion to be fitted in the groove in the foregoing embodiments, but not limited thereto. The engaging side may be formed as a protrusion portion and the side of the portion to be engaged may be formed as a groove or recess portion. Additionally, the engaging portion and the portion to be engaged may be provided plurally at the ring body and hub, respectively.

Further, a through hole, through which the ring body is passed, may be provided at the hub body. The through hole is preferably formed at a flange-shaped guide portion serving as a depressing indicator in case where the ring body slidingly moves on the outer peripheral surface of the stabilizing section. In case where the ring body slidingly moves on the inner peripheral surface of the stabilizing section or on the outer peripheral surface of the adjustment section, the through hole is disposed at the end face of the hub body. By this, the axial length of the ring body can be well secured.

EXPLANATIONS OF LETTERS OR NUMERALS 1, 21, 31: Drug injection device, 2: Injection needle assembly, 3: Syringe, 3a: Fitting portion, 5: Needle tube, 5a: Blade face, 6: Hub, 7: Puncture speed securing member, 8: Needle tip, 10: Hub body, 11: Fixing section, 12, 22: Adjustment section, 12a, 22a, 32a: Needle projection surface, 13: Stabilizing section, 13a: End face, 13b, 22b, 32b: Portion to be engaged, 15, 25, 35: Ring body, 16, 26, 36: Engaging portion, 16a, 26a: Groove portion, 17: Inner flange portion, 18: Abutment face, 19: Guide portion (depressing indicator), 19a: Contact surface, 32c: Portion to be fitted, 36: Fitting portion, B: Bevel length, L: Projection length, S, $S_2$: Distance of from the peripheral edge of needle projection surface or ring body to the peripheral surface of needle tube, T, $T_2$: Distance of from the inner wall surface of stabilizing section or the peripheral edge of ring body to the outer peripheral surface of adjustment section, x: Guide portion length, y: Guide portion height, d: Inner diameter.

What is claimed is:

1. An injection needle assembly comprising:
a needle tube having a needle tip capable of being punctured in a living body;
a hub holding said needle tube;
an adjustment section disposed around said needle tube and having a needle projection surface from which said needle tip of said needle tube projects;
a stabilizing section extending from said hub and disposed to surround said needle tube, said stabilizing section having an end face which contacts with the skin when said needle tube is punctured in the living body; and
a puncture speed securing member disposed, at said adjustment section or said stabilizing section movably in an axial direction of said needle tube, for securing a speed and depressing force upon puncturing said needle tube in the living body by contacting the skin ahead of said needle tip of said needle tube when said needle tube is punctured in the living body.

2. The injection needle assembly as defined in claim 1, characterized in that
said puncture speed securing member is formed in ring form and has an engaging portion engaging a portion to be engaged, the portion to be engaged provided on at least a portion of an outer peripheral surface of said adjustment section, an inner peripheral surface of said stabilizing section and an outer peripheral surface of said stabilizing section, and said engaging portion and said portion to be engaged are disengaged when a force greater than a given depressing force is inputted.

3. The injection needle assembly as defined in claim 2, characterized in that
an outer peripheral surface of said stabilizing section or said puncture speed securing member is provided with a depressing indicator that has a stepped surface made vertical to said outer peripheral surface.

4. The injection needle assembly as defined in claim 3, characterized in that
said depressing indicator is a flange, which projects vertically from said outer peripheral surface of said stabilizing section or said puncture speed securing member toward a radial outer side.

5. The injection needle assembly as defined in claim 1, characterized in that
said puncture speed securing member is set at a first position, wherein a contact face contacting the living body covers said needle tip of said needle tube, in a state prior to the puncture of said needle tube in the living body and moves to a second position, wherein said needle tip of said needle tube is exposed and said contact face is situated on the same plane surface as said end face of said stabilizing section, when said needle tube is punctured in the living body.

6. The injection needle assembly as defined in claim 5, characterized in that
an outer peripheral surface of said stabilizing section or said puncture speed securing member is provided with a depressing indicator that has a stepped surface made vertical to said outer peripheral surface.

7. The injection needle assembly as defined in claim 6, characterized in that
said depressing indicator is a flange, which projects vertically from said outer peripheral surface of said stabilizing section or said puncture speed securing member toward a radial outer side.

8. The injection needle assembly as defined in claim 1, characterized in that
an outer peripheral surface of said stabilizing section or said puncture speed securing member is provided with a depressing indicator that has a stepped surface made vertical to said outer peripheral surface.

9. The injection needle assembly as defined in claim 8, characterized in that
said depressing indicator is a flange, which projects vertically from said outer peripheral surface of said stabilizing section or said puncture speed securing member toward a radial outer side.

10. A drug injection device comprising:
a needle tube having a needle tip capable of being punctured in a living body;
a hub holding said needle tube;
an adjustment section disposed around said needle tube and having a needle projection surface from which a needle tip of said needle tube projects;
a syringe connected to said hub;
a stabilizing section extending from said hub and disposed to surround said needle tube, said stabilizing section having an end face which contacts with the skin when said needle tube is punctured in the living body; and
a puncture speed securing member disposed, at said adjustment section or said stabilizing section movably in an axial direction of said needle tube, for securing a speed and depressing force upon puncturing said needle tube in the living body by contacting the skin ahead of said needle tip of said needle tube when said needle tube is punctured in the living body.

11. The injection needle assembly as defined in claim 2, characterized in that
said puncture speed securing member is set at a first position, wherein a contact face contacting the living body covers said needle tip of said needle tube, in a state prior to the puncture of said needle tube in the living body and moves to a second position, wherein said needle tip of said needle tube is exposed and said contact face is situated on the same plane surface as said end face of said stabilizing section, when said needle tube is punctured in the living body.

* * * * *